United States Patent
Gros et al.

(10) Patent No.: US 6,727,378 B2
(45) Date of Patent: Apr. 27, 2004

(54) PROCESS FOR THE PRODUCTION OF A PHOSPHORUS-CONTAINING ORGANIC COMPOUND

(75) Inventors: Georges Gros, Antony (FR); Michel Garrait, Charly (FR); Patrick Rey, Mourèze (FR); Jacques Taillades, Clapiers (FR)

(73) Assignee: Adisseo France S.A.S., Antony (FR)

( * ) Notice: Subject to any disclaimer, the term of this patent is extended or adjusted under 35 U.S.C. 154(b) by 4 days.

(21) Appl. No.: 10/147,064

(22) Filed: May 17, 2002

(65) Prior Publication Data

US 2002/0173671 A1 Nov. 21, 2002

(30) Foreign Application Priority Data

May 18, 2001 (EP) ............................................. 01420114

(51) Int. Cl.[7] ............................... C07F 9/08; C07F 9/38; C07F 9/53
(52) U.S. Cl. ............................. 558/87; 562/8; 556/14; 556/15
(58) Field of Search ............................... 568/13, 14, 15; 562/11, 8; 558/70, 87

(56) References Cited

U.S. PATENT DOCUMENTS

| | | |
|---|---|---|
| 2,724,718 A | 11/1955 | Stiles et al. |
| 4,521,348 A | 6/1985 | Finke et al. |
| 6,090,968 A | 7/2000 | Horold et al. |

FOREIGN PATENT DOCUMENTS

| | | |
|---|---|---|
| EP | 0 969 008 | 1/2000 |
| WO | WO 92/12985 | 8/1992 |

OTHER PUBLICATIONS

CA:105:97563 abs of Tetrahedron Letters by Osowska–Pacewicka et al 41(20) pp 4717–4725 1985.*
CA:126:264208 abs of DE 19609336 Mar. 1997.*
CA:133:362841 abs of EP1055677 Nov. 2000.*
CA:97:144932 abs of Angewandte Chemie by Sander et al 94(7) pp 562–562 1982.*
CA:61:47986 abs of J Org Chem by Inukai et al 29(8) pp 224–226 1964.*
CA:111:6850 abs of Journal of Chemical Society , Perkin Transactions 2: Physical Organic Chemistry by Baban et al (7) pp 1195–1200 1988.*
Derwent Abstract of DE 2849003, WPI Acc No: 1980–38622C/198022 1980.
Derwent Abstract of DE 2516343, WPI Acc No: 1976–83339X/*197645* 1976.
Derwent Abstract of DE 2516341, WPI Acc No: 1976–83337X/*197645* 1976.

* cited by examiner

*Primary Examiner*—Jean F. Vollano
(74) *Attorney, Agent, or Firm*—Finnegan, Henderson, Farabow, Garrett & Dunner, LLP

(57) ABSTRACT

A process for the production of an organic phosphorus-containing product, which comprises reacting a phosphorus-containing oxide with an unsaturated hydrocarbon in the presence of a boron-containing compound at a temperature of less than or equal to 50° C.

14 Claims, No Drawings

PROCESS FOR THE PRODUCTION OF A PHOSPHORUS-CONTAINING ORGANIC COMPOUND

The present invention relates to a process for the production of phosphorus-containing organic compounds by the catalysed reaction between a phosphorus-containing oxide and an unsaturated hydrocarbon.

The Pudovik reaction is one of the most versatile pathways for the formation of carbon-phosphorus bonds and involves the addition of compounds containing a labile P—H bond with unsaturated systems such as alkenes, alkynes, carbonyls and imines as shown below:

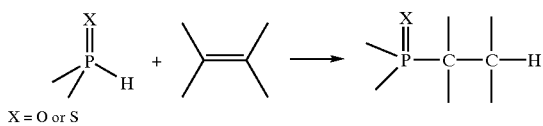

The products of the reaction find significant applications in a wide range of areas, for example industrial, biological, and chemical synthetic uses. The Pudovik reaction can progress via a radical and/or an ionic mechanism. It appears in the literature that the difference in the Pudovik reaction mechanisms depends upon the nature of the unsaturated substrates. In fact, when the unsaturated substrate is an unsaturated system having a nucleophilic character, the mechanism is preferentially radical. In this case, photoactivation or chemical activation (peroxides, AIBN) is the most efficient method.

A problem associated with such methods is that the reaction time is long and experimental conditions are mostly drastic. Furthermore, the regioselectivity of the addition can be weak. More recently, ultrasound-induced radical reaction in homogeneous medium has been used. Indeed, when the unsaturated compound contains an electron-withdrawing substituent, the main mechanism is ionic. Diethylamine or potassium hydroxide is generally used and recently a tetramethylguanidine-catalyst has been employed efficiently under mild conditions. In the presence of free radical initiators or under photochemical or ultrasound irradiation in homogeneous medium, the phosphorylated reagents ($R_2P(O)H$) add to the double bond by a free radical mechanism and the orientation is anti-Markovnikov. In basic medium, the addition occurs by nucleophilic attack of phosphorus anions to olefins by a Michael type mechanism and the orientation is also anti-Markovnikov.

It is known to produce phosphorus-containing organic compounds through the reaction of a phosphine oxide and an unsaturated hydrocarbon as is evidenced by DE 2849003, DE 2516341 and DE 2516343. The reactions used in the processes of these patent applications are carried out at a temperature in excess of 100° C. and require an initiator. Furthermore, unwanted by-products are produced which have to be separated at the end of the synthesis route, thereby adding an additional step to the process.

We have found that phosphorus-containing organic compounds can be prepared by a simple synthesis route that does not produce substantial undesired by-products and can be carried out under less severe reaction conditions.

Accordingly, the present invention provides a process for the production of organic phosphorus-containing products having the general formula (I)

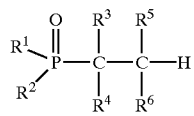

wherein:
$R^1$ and $R^2$ are each independently alkyl, aryl, hydroxy, O-alkyl or O-aryl;
$R^3$, $R^4$, $R^5$ and $R^6$ are each independently hydrogen, alkyl, aryl, $R^7OH$, $R^8CN$, $R^9NXY$, or $CH(CH_2)_nOR^{10}OR^{11}$;
$R^7$ is $CH_2$, $CH(CH_2)_n$ or $CH(OH)(CH_2)_n$;
$R^8$ is $CH_2$, $CH(CH_2)_n$ or $CH(OAc)(CH_2)_n$ and,
$R^9$ is $CH(CH_2)_n$ or $CHCO_2R^{12}$, where $R^{12}$ is hydrogen, alkyl or aryl;
X and Y are independently selected from hydrogen, alkyl, aryl or ester;
$R^{10}$ and $R^{11}$ are the same or different and may be hydrogen, alkyl or aryl or the two groups may be linked by $(CH_2)_n$ to form a cyclic ring; and
n is from 0 to 12,
which comprises reacting a phosphorus-containing oxide of general formula (II)

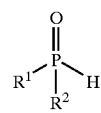

wherein the various symbols are as defined above with an unsaturated hydrocarbon of general formula (III)

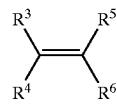

wherein the various symbols are as defined above, in the presence of a boron-containing compound and at a temperature of less than or equal to 50° C.

The process of the present invention provides the advantage over the known prior art in that the reaction conditions are less severe and there are substantially no unwanted by-products.

The process of the present invention involves reacting a phosphorus-containing oxide of general formula (II) with a unsaturated hydrocarbon. $R^1$ and $R^2$ of compound (II) may be the same or may be different and may be selected from alkyl, aryl, hydroxy, O-alkyl or O-aryl. Where $R^1$ or $R^2$ is alkyl or O-alkyl, the alkyl group may be $C_1$ to $C_6$ alkyl, for example $C_1$ to $C_3$ alkyl, for instance methyl. Where $R^1$ or $R^2$ is aryl or O-aryl, the aryl group may be phenyl or substituted phenyl, for example halo phenyl, alkoxy phenyl or alkyl phenyl. An example compound for use in the present process is where $R^1$ and $R^2$ are independently methyl or phenyl.

As regards the unsaturated hydrocarbon compound, this compound may be, for example, an alkene, an allylic acid, an allylic alcohol, an allylic-alpha-acetoxy nitrile or an alpha amino acid vinyl such as D or L-vinylglycine. In particular, $R^3$, $R^4$, $R^5$ and $R^6$ of general formula (III) may be the same or may be different and may be selected from H, alkyl, aryl, $R^7OH$ or $R^8CN$, $R^9NXY$, or $CH(CH_2)_nOR^{10}OR^{11}$. Where $R^3$, $R^4$, $R^5$ and/or $R^6$ is alkyl, this may be $C_1$ to $C_{12}$ alkyl, for example $C_1$ to $C_6$ alkyl, for instance methyl. Where $R^3$, $R^4$, $R^5$ and/or $R^6$ is an alcohol functionality of the formula $R^7OH$, $R^7$ is $CH_2$, $CH(CH_2)_n$ or $CH(OH)(CH_2)_n$ where n is from 0 to 12, for example from 1 to 6. Where $R^3$, $R^4$, $R^5$ and/or $R^6$ is a cyano functionality of the formula $R^8CN$, $R^8$ is $CH_2$, $CH(CH_2)_n$ or $CH(OAc)(CH_2)_n$, where n is from 0 to 12, for example from 1 to 6. Where $R^3$, $R^4$, $R^5$ and/or $R^6$ is a nitrogen functionality of the formula $R^9NXY$, $R^9$ is, for example, $CHCO_2R^{12}$, where $R^{12}$ may be selected from hydrogen, alkyl or aryl, and X and Y are independently selected from hydrogen, alkyl, aryl or ester. Where $R^3$, $R^4$, $R^5$ and/or R is $CH(CH_2)_nOR^{10}OR^{11}$, $R^{10}$ and $R^{11}$ may be the same or different and may be hydrogen, alkyl or aryl or the two groups may be linked by $(CH_2)_n$ to form a cyclic ring. The alkyl and aryl groups and n are as herein before defined.

The phosphorus-containing oxide and the unsaturated hydrocarbon may be reacted in any suitable amount to allow reaction. The amount of oxide to unsaturated hydrocarbon may be, for example, in a ration 2 to 1 or 1 to 1, for instance the two reactants may be present in stoichiometric amounts.

The process of the present invention is carried out in the presence of a boron compound. Suitable boron compounds are alkyl boranes such as methyl, ethyl and propyl. An example compound is triethyl borane. The boron compound may be present in an amount of, for example, from 1 to 30% molar concentration, for instance from 5 to 20%.

The process may be carried out in the presence of a solvent. Suitable solvents include alcohols, for example methanol; hydrocarbons, for example hexane; nitriles, for example acetonitrile; and ketones, for example acetone. The solvent in the process may be, for example, an alcohol such as methanol. The solvent may be present in the reaction medium in an amount of, for example, from 0 to 150 equivalents, for instance from 20 to 60 equivalents.

The process is carried out at a temperature of less than or equal to 50° C., for example less than or equal to 20° C. For instance, the process can be operated at a temperature of from (minus) –20 to (plus) +20° C., for example from –15 to +20° C.

The compounds of formula (I) have one or more of the following uses: use as intermediates for the manufacture of flameproofing agents, flame retardants for polymers, solvents for dyes, extractants for metals from aqueous solutions, and use as biologically active compounds having bactericidal, fungicidal or herbicidal action.

The process of the present invention will now be illustrated with reference to the following examples:

EXAMPLE 1

Synthesis of (3-hydroxy-butyl)-diphenylphosphine Oxide ($Ph_2P(O)CH_2CH_2CH(OH)CH_3$ 0.52 g (2.57 mmol) diphenyl phosphine oxide and 0.20 g (2.17 mmol) of but-3-ene-2-ol were placed in a closed stirred tank reactor containing 5 g (156 mmol) of methanol at 20° C. The mixture was agitated until all of the phosphine oxide had dissolved. 0.8 ml (0.8 mmol) of molar triethylborane was slowly added. The gas formed was eliminated and the methanol allowed to evaporate. The resulting liquid was washed with 30 ml of ether and the ether phase then washed with 10 ml of water. The resulting mixture was decanted and the ether phased dried with sodium sulphate, followed by filtration and evaporation. The product obtained gave a 80% yield and was identified by $^1H$ and $^{31}P$ NMR as (3-hydroxy-butyl)-diphenylphosphine oxide.

EXAMPLE 2

Synthesis of Dodecyl-diphenylphosphine Oxide ($Ph_2P(O)CH_2(CH_2)_9CH_3$)

The procedure as for Example 1 was repeated using 0.51 g (2.52 mmol) of diphenylphosphine oxide, 0.46 g (2.52 mmol) of 1-dodecene. These reactants were added to 6 g (180 mmol) of methanol. 0.3 ml (0.3 mmol) of molar triethylborane was slowly added to the mix. The yield of product obtained was 95% and was identified by $^1H$ and $^{31}P$ NMR as dodecyl diphenylphosphine oxide.

EXAMPLE 3

Synthesis of (3-acetoxy-3-cyano-propyl)-diphenylphosnhine Oxide ($Ph_2P(O)CH_2CH_2CH(OAc)CN$)

The procedure as for Example 1 was repeated using 0.50 g (2.47 mmol) of diphenyl phosphine oxide, 0.34 g (2.71 mmol) of 2-acetoxy-but-3-enenitrile and at a temperature of 10° C. The reactants were added to 7 g (218 mmol) of methanol. 0.5 ml (0.5 mmol) of molar triethylborane was slowly added to the mix. The yield of product obtained was 65% and was identified by $^1H$ and $^{31}P$ NMR as (3-acetoxy-3-cyano-propyl)-diphenylphosphine oxide.

EXAMPLE 4

Synthesis of (3,4-dihydroxy-butyl)-diphenylphosphine Oxide ($Ph_2P(O)CH_2CH_2CH(OH)CH_2OH$)

The procedure as for Example 1 was repeated using 0.50 g (2.47 mmol) of diphenylphosphine oxide and 0.23 g (2.61 mmol) of 3-butene-1,2-diol. The reactants were added to 6 g (180 mmol) of methanol. 0.5 ml (0.5 mmol) of molar triethylborane was slowly added to the mix. The yield of product obtained was 85% and was identified by $^1H$ and $^{31}P$ NMR as (3,4-dihydroxy-butyl)-diphenylphosphine oxide.

EXAMPLE 5

Synthesis of Phenyl Dodecylphosphinic Acid (Ph(OH)P(O)CH_2CH_2(CH)_9CH_3)

The procedure as for Example 1 was repeated using 1.0 g (7.0 mmol) of phenyl phosphinic acid, 1.2 g (7.0 mmol) of 1-dodecene and at a temperature of minus 15° C. The reactants were added to 5 g (156 mmol) of methanol. 0.8 ml (0.8 mmol) of molar triethylborane was slowly added to the mix. The yield of product obtained was 92% and was identified by $^1H$ and $^{31}P$ NMR as phenyl dodecylphosphinic acid.

EXAMPLE 6

Synthesis of (3-hydroxy-butyl)-phenyl Dodecylphosphinic Acid (Ph(OH)P(O)CH_2CH_2CH(OH)CH_3)

The procedure as for Example 5 was repeated using 1.08 g (7.6 mmol) of phenylphosphinic acid, 0.45 g (6.2 mmol) of but-3-en-2-ol and at a temperature of minus 15° C. The reactants were added to 5 g (156 mmol) of methanol. 0.8 ml (0.8 mmol) of molar triethylborane was slowly added to the mix. The yield of product obtained was 84% and was identified by $^1H$ and $^{31}P$ NMR as (3-hydroxy-butyl) phenylphosphinic acid.

EXAMPLE 7

Synthesis of O',O'di-ethyl Dodecylphosphonate ($Et_2OP(O)CH_2CH_2(CH_2)_9CH_3$)

The procedure as for Example 1 was repeated using 1.06 g (7.7 mmol) of diethyl phosphite, 1.1 g (6.53 mmol) of 1-dodecene and at a temperature of minus 15° C. The reactants were added to 5 g (156 mmol) of methanol. 1.0 ml (1.0 mmol) of molar triethylborane was slowly added to the mix. The yield of product obtained was 37% and was identified by $^1$H and $^{31}$P NMR as O',O'di-ethyl dodecylphosphonate.

EXAMPLE 8

Synthesis of Dodecyl-diphenylphosphine Oxide $(Ph_2P(O)CH_2(CH_2)_9CH_3)$

The procedure as for Example 1 was repeated using 0.31 g (1.53 mmol) of diphenylphosphine oxide, 1.02 g (6.06 mmol) of 1-dodecene. The mixture was agitated until all of the phosphine oxide had dissolved. 0.3 ml (0.3 mmol) of molar triethylborane was slowly add to the mix. The reaction temperature was maintained at 20° C. The yield of the product obtained was 78% and was identified by $^1$H and $^{31}$P NMR as dodecyl-diphenylphosphine oxide.

EXAMPLE 9

Synthesis of (3-hydroxy-butyl)-diphenylphosphine Oxide $(Ph_2P(O)CH_2CH_2CH(OH)CH_3)$ The procedure as for Example 1 was repeated using 0.39 g (1.92 mmol) of diphenylphosphine oxide, 1.02 g (14.14 mmol) of but-3-en-2-ol. 0.25 ml (0.25 mmol) of molar triethylborane was slowly add to the mix. The reaction temperature was maintained at 20° C. The yield of the product obtained was 58% and was identified by $^1$H and $^{31}$P NMR as (3-hydroxy-butyl)-diphenylphosphine oxide.

EXAMPLE 10

Synthesis of (3,4-dihyroxybutyl)-phenylphosphinc Acid $(Ph(OH)P(O)CH_2CH_2CH(OH)CH_2OH)$ The procedure as for Example 5 was repeated using 1.08 g (7.60 mmol) of phenylphosphonic acid, 1.32 g (14.68 mmol) of 3-butene-1,2-diol and at a temperature of minus 10° C. The reactants were added to 5 g (156 mmol) of methanol. 0.70 ml (0.7 mmol) of molar triethylborane was slowly added to the mix. The yield of product obtained was 62% and was identified by $^1$H and $^{31}$P NMR as (3,4-dihyroxybutyl)-phenylphosphinc acid.

EXAMPLE 11

Synthesis of (2-methyl-propan-1-ol)-phenylphosphinc Acid $(Ph(OH)P(O)CH_2CH(_3)CH_2OH)$ The procedure as for Example 5 was repeated using 1.0 g (7.03 mmol) of phenylphosphonic acid, 0.25 g (3.46 mmol) of 2-methyl-prop-2-en-1-ol and at a temperature of minus 10° C. The reactants were added to 5 g (156 mmol) of methanol. 0.70 ml (0.7 mmol) of molar triethylborane was slowly added to the mix. The yield of product obtained was 57% and was identified by 1H and $^{31}$P NMR as (2-methyl-propan-1-ol)-phenylphosphinc acid.

EXAMPLE 12

Synthesis of (3-hydroxy-3-methyl-butyl)-phenylphosphinc Acid $(Ph(OH)P(O)CH_2CH_2C(CH_3)_2OH)$ The procedure as for Example 5 was repeated using 0.97 g (6.82 mmol) of phenylphosphonic acid, 0.59 g (6.85 mmol) of 2-methylbut-3-en-2-ol and at a temperature of minus 10° C. The reactants were added to 5 g (156 mmol) of methanol. 0.60 ml (0.6 mmol) of molar triethylborane was slowly added to the mix. The yield of product obtained was 75% and was identified by $^1$H and $^{31}$P NMR (3-hydroxy-3-methyl-butyl)-phenylphosphinc acid.

We claim:

1. A process for the production of an organic phosphorus-containing product having the formula (I)

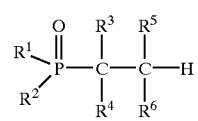

(I)

wherein:

$R^1$ and $R^2$ are each independently alkyl, aryl, hydroxy, O-alkyl or O-aryl;

$R^3$, $R^4$, $R^5$ and $R^6$ are each independently hydrogen, alkyl, $R^7$OH, $R^8$CN, $R^9$NXY or $CH(CH_2)_nOR^{10}OR^{11}$, where $R^7$ is $CH_2$, $CH(CH_2)_n$ or $CH(OH)(CH_2)_n$;

$R^8$ is $CH_2$, $CH(CH_2)_n$ or $CH(OAc)(CH_2)_n$ and, $R_9$ is $CH(CH_2)_n$ or $CHCO_2R^{12}$, where $R^{12}$ is hydrogen, alkyl or awl, and X and Y are independently selected from hydrogen, alkyl, aryl or ester;

$R^{10}$ and $R^{11}$ are the same or different and are hydrogen, alkyl or aryl or, alternatively, the two groups $R^{10}$ and $R^{11}$ are linked by $(CH_2)_n$ to form a cyclic ring; and n is from 0 to 12, which comprises reacting a phosphorus-containing oxide of formula (II)

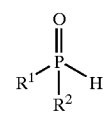

(II)

wherein $R^1$ and $R^2$ are as defined ahoy; with an unsaturated hydrocarbon of formula (III)

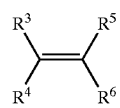

(III)

wherein $R^3$, $R^4$, $R^5$ and $R^6$ are as defined above, in the presence of an alkyl borane and at a temperature of less than or equal to 50°.

2. A process as claimed in claim 1, in which the alkyl borane is a $C_1$ to $C_3$ alkyl borane.

3. A process as claimed in claim 2, in which the alkyl borane is triethyl borane.

4. A process as claimed in claim 1, which is carried out at a temperature of less than or equal to 20° C.

5. A process as claimed in claim 1, which is carried out at a temperature of from −20° C. to +20° C.

6. A process as claimed in claim 1, which is carried out in the presence of a solvent.

7. A process as claimed in claim 6, in which the solvent is a hydrocarbon solvent, an alcohol, a ketone or a nitrile.

8. A process as claimed in claim 7, in which the solvent is methanol.

9. A process as claimed in claim 1, wherein $R^1$ and $R^2$ are phenyl and $R^3$, $R^4$, $R^5$ and $R^6$ are hydrogen.

10. A process as claimed in claim 1, wherein $R^1$ and $R^2$ are independently alkyl and $R^3$, $R^4$, $R^5$ and $R^6$ are hydrogen.

11. A process as claimed in claim 1, wherein $R^1$ and $R^2$ are ethyl and $R^3$, $R^4$, $R^5$ and $R^6$ are hydrogen.

12. A process as claimed in claim 1, wherein n is from 1 to 6.

13. A process as claimed in claim 1, wherein the amount of reactant phosphorus-containing oxide of formula (II) to reactant unsaturated hydrocarbon of formula (III) is in a ratio of 2 to 1.

14. A process as claimed in claim 1, wherein the amount of reactant phosphorus-containing oxide of formula (II) to reactant unsaturated hydrocarbon of formula (III) is in a ratio of 1 to 1.

* * * * *

UNITED STATES PATENT AND TRADEMARK OFFICE
CERTIFICATE OF CORRECTION

PATENT NO. : 6,727,378 B2
DATED : April 27, 2004
INVENTOR(S) : Georges Gros et al.

It is certified that error appears in the above-identified patent and that said Letters Patent is hereby corrected as shown below:

Column 6,
Line 20, after "alkyl," insert -- aryl, --.
Line 26, "awl," should read -- aryl, --.
Line 42, "ahoy;" should read -- above, --.
Line 53, "50°." should read -- 50° C. --.

Signed and Sealed this

Thirteenth Day of July, 2004

JON W. DUDAS
*Acting Director of the United States Patent and Trademark Office*